United States Patent
Muny

(10) Patent No.: US 9,046,459 B2
(45) Date of Patent: Jun. 2, 2015

(54) TAPE TEST REMOVAL DEVICE

(71) Applicant: Keith Muny, Rocky River, OH (US)

(72) Inventor: Keith Muny, Rocky River, OH (US)

(73) Assignee: Cheminstruments, Inc., Fairfield, OH (US)

(*) Notice: Subject to any disclaimer, the term of this patent is extended or adjusted under 35 U.S.C. 154(b) by 0 days.

(21) Appl. No.: 14/100,591

(22) Filed: Dec. 9, 2013

(65) Prior Publication Data

US 2014/0157908 A1    Jun. 12, 2014

Related U.S. Application Data

(60) Provisional application No. 61/735,741, filed on Dec. 11, 2012.

(51) Int. Cl.
*G01N 19/04* (2006.01)
*G01N 3/08* (2006.01)

(52) U.S. Cl.
CPC ........ *G01N 19/04* (2013.01); *G01N 2203/0091* (2013.01)

(58) Field of Classification Search
CPC .................. G01N 19/04; G01N 2203/0091
USPC .................. 73/827, 150 A, 150 R, 9
See application file for complete search history.

(56) References Cited

U.S. PATENT DOCUMENTS

| | | | |
|---|---|---|---|
| 6,513,374 B2* | 2/2003 | Goh et al. | 73/150 A |
| 7,913,552 B2* | 3/2011 | Himmelbauer et al. | 73/150 A |
| 2002/0100334 A1* | 8/2002 | Goh et al. | 73/835 |
| 2009/0114006 A1* | 5/2009 | Himmelbauer et al. | 73/150 A |
| 2013/0199285 A1* | 8/2013 | Murtonen et al. | 73/150 R |

* cited by examiner

*Primary Examiner* — Lisa Caputo
*Assistant Examiner* — Jonathan Dunlap
(74) *Attorney, Agent, or Firm* — Fay Sharpe LLP; James E. Scarbrough

(57) ABSTRACT

A tape test removal device has an elongated housing having a first end and a second end; a shuttle which slides along a longitudinal axis of the housing and is disposed within the housing; a biasing member adjacent the first end of the housing and positioned adjacent the shuttle member; the biasing member is secured in a first, compressed conformation; and a clip extending from the shuttle to hold a portion of a tape to be tested.

11 Claims, 2 Drawing Sheets

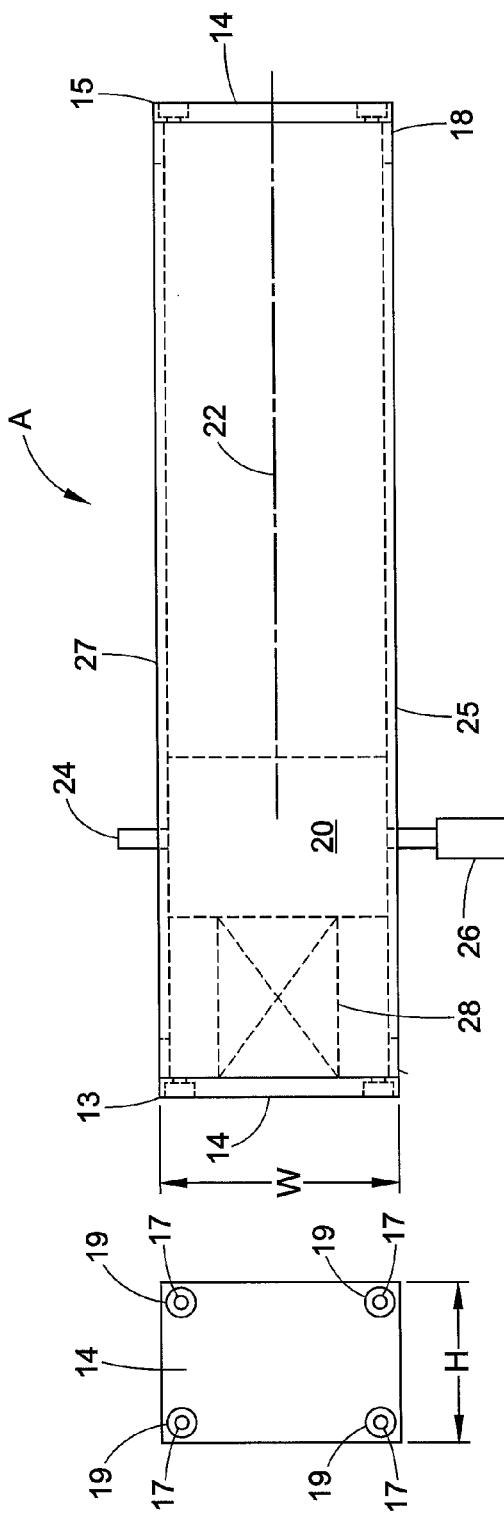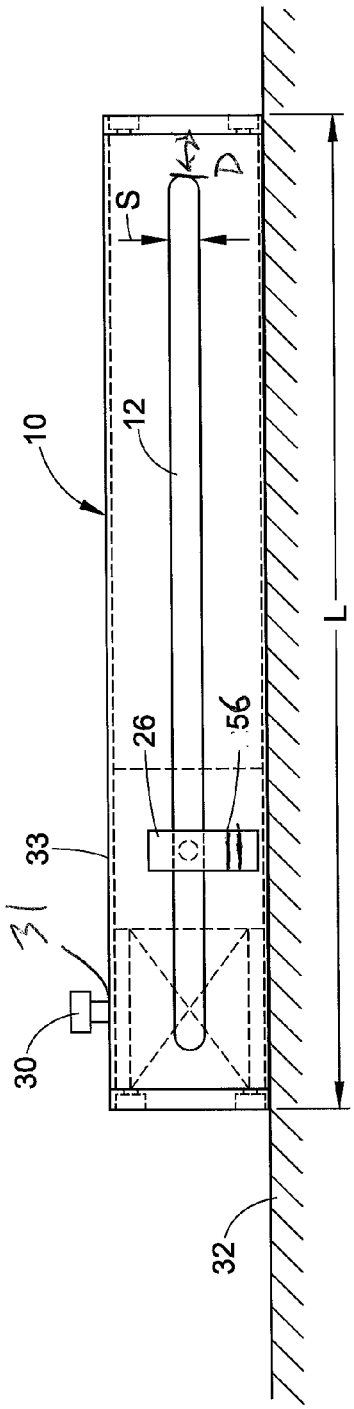

TAPE TEST REMOVAL DEVICE

CLAIM OF PRIORITY

This application claims priority from Provisional Application Ser. No. 61/735,741 filed on Dec. 11, 2012, which is hereby incorporated by reference in its entirety.

BACKGROUND OF THE DISCLOSURE

The present disclosure relates to a tape test removal device. More particularly, it relates to a tape test removal device which mechanizes the removal process relating to the manual tape test method of removing tape and measuring the adhesion of the tape on the work surface such as outlined in ASTM D3359-09 which is incorporated by reference herein.

When applying a coating such as an adhesive, ink, or paint, for example, to a substrate, it is typically important that the coating be adequately adhered to the surface of the substrate to which it is applied. This is especially important in industries such as printing, and painting industries. During the manufacturing process in these types of industries, many factors can affect the adhesive strength of the bond between the inks, paints, and other coatings, and the surface of the substrate. Thus, it is necessary to test the adhesion during the manufacturing/printing process to confirm that a desired level of adhesion is obtained. A standard test, commonly termed a tape test and described in ASTM test standards D3359 and F1842, as well as other test standards such as ISO 2409, for example, have been developed for evaluating the adhesive strength of the bond between the coatings and the surface of the substrate.

The tape test is typically performed by applying a strip of tape to the surface, removing it, and visually evaluating the amount of coating that has been removed by the tape. In the standard test, the tape is both applied and removed by hand.

A problem with existing methods is that since they are manually performed they are not completely accurate and easily repeatable.

Thus, there is a need for an improved test method which includes applying a standard tape sample to a printed surface, then a mechanical process for removing the tape. A reporting process is then associated with the removal of the tape.

SUMMARY OF THE DISCLOSURE

The present disclosure relates to a tape test removal device. More particularly, it relates to a tape test removal device which mechanizes the removal process relating to the manual tape test method as outlined in ASTM D3359-09. The tape test removal device provides for consistency and repeatability of results while also providing a low cost and easy method for measuring removal of tape from a surface.

One aspect of the tape test removal device is to standardize the removal process of a tape sample from a surface. Another aspect of the disclosure is the device is very simple to operate and a low cost mechanism.

Still another aspect of the disclosure is the device standardizes the removal angle of the sample at a virtually constant 180° angle. Another aspect of the disclosure is it also consistently removes the sample at a repeatable rate. The device is rather compact and lightweight and very portable. The low cost of the device will allow a user to purchase multiple units, which will allow the user to locate devices in all of the necessary places that would need this type of product verification. The ability to have this quick reference will assist the user in quickly adjusting the manufacturing process to produce a high quality product.

In accordance with one aspect of the disclosure, a tape test removal device has an elongated housing having a first end and a second end; a shuttle which slides along a longitudinal axis of the housing and is disposed within the housing; a biasing member adjacent the first end of the housing and positioned adjacent the shuttle member; the biasing member is secured in a first, compressed conformation; and a clip extending from the shuttle to hold a portion of a tape to be tested.

In accordance with another aspect of the disclosure, a method of testing tape removal from a work surface includes the steps of bending an end of the tape to form a tab on the end of the tape by having an adhesive side of the tape folded on itself; positioning a tape test removal adhesive onto the work surface; applying pressure to the device to firmly position it onto the work surface; securing the tab within a clip extending from the device; flipping a latch on the device to release a compression spring therein; moving a shuttle, holding the clip, adjacent the compression spring by expansion of the spring from a first end to a second end of the device; pulling the tape at a consistent 180 degree angle with respect to the work surface as the shuttle moves from the first end to the second end.

The above aspects, as well as other aspects of the disclosure, will become readily apparent to those skilled in the art from the following detailed description of an embodiment of the disclosure when considered in the light of the accompanying drawings.

BRIEF DESCRIPTION OF THE DRAWINGS

FIG. 1A is a top plan view of a tape test removal device for testing the adhesion of a coating to a surface of a substrate according to an embodiment of the disclosure;

FIG. 1B is a side elevational view of a tape test removal device of FIG. 1A;

FIG. 1C is an end elevational view of the end cap of the device of FIG. 1A; and

DETAILED DESCRIPTION OF THE DISCLOSURE

Figure 2:
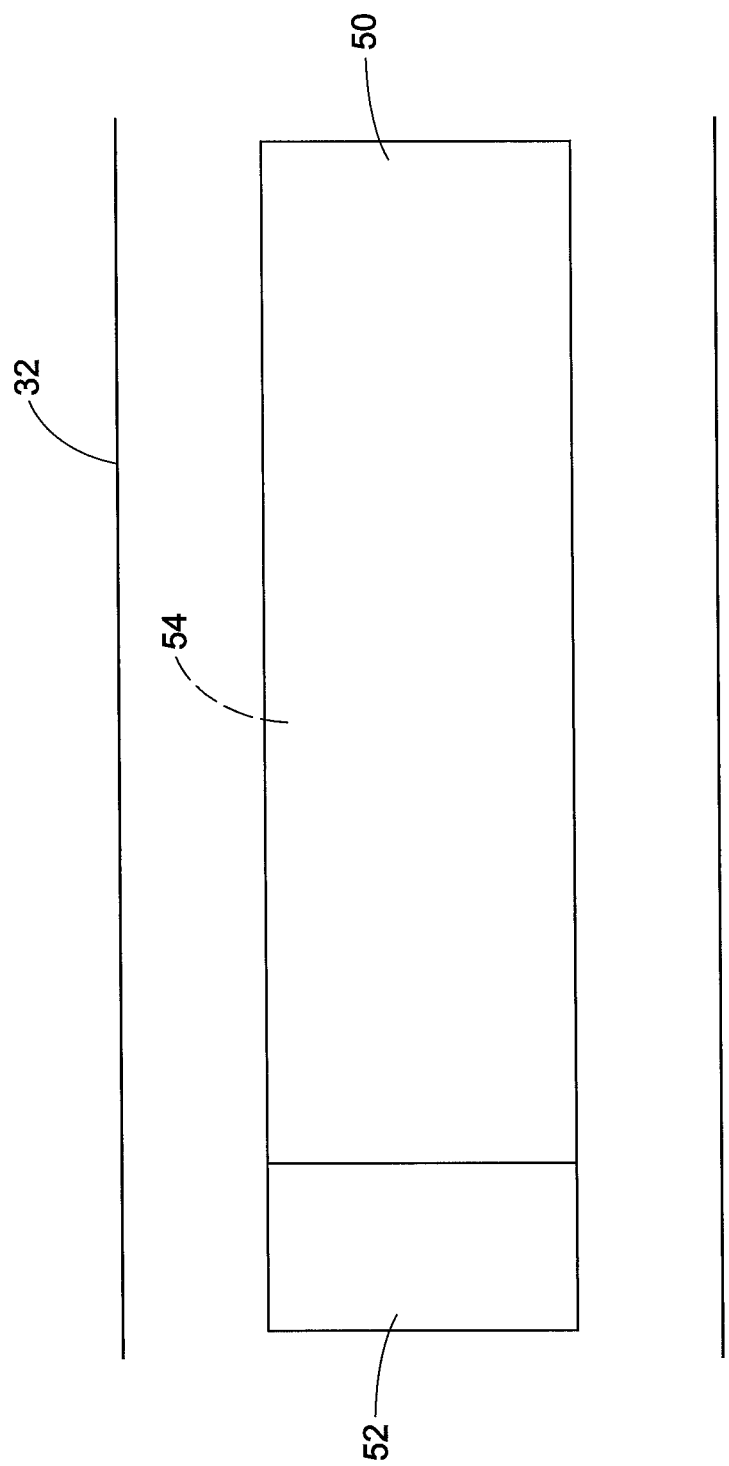
FIG. 2 is a top plan view of a tape to be removed from a work surface.

The present disclosure relates to a tape test removal device. More particularly, it relates to a tape test removal device which mechanizes the removal process relating to the tape test method as outlined in ASTM D3359-09 which is hereby incorporated by reference.

The purpose of the device is to standardize the removal process of a tape sample from a test surface. The device is compact, lightweight, simple to operate and portable. It standardizes the removal angle of the tape sample at a consistent 180° angle. It also consistently removes the sample at a repeatable rate.

Referring specifically now to FIGS. 1A-1C, a tape test removal device A in accordance with a preferred embodiment of the disclosure is shown. A rectangular tube or housing 10 forms the main framework of the device. Approximate dimensions of the tube are a height H of about 2 inches high and a width W of about 3 inches wide and a length L of about 12 inches long. A slot 12, about ⅜ inches in height S, extends nearly the entire length L of the tube between first end 13 and second end 15 of the tube. The slot does not extend from dimension D, about 0.5 inches at either end of the tube. The tube has an end cap 14 secured to each opposed end 13, 15 to enclose the opposed ends of the tube. The tube is preferably made of material such as aluminum, but other materials are contemplated by the disclosure. End cap 16 is secured to opposed ends 13, 15 via fasteners 17 in openings 19.

A plastic shuttle 20 rides inside of the tube along a longitudinal axis 22 of the tube. The shuttle dimensions preferably approximate the interior cross sectional internal dimensions of the tube. That is, the length of the shuttle is such that it allows the shuttle to traverse back and forth smoothly within the tube. The shuttle has a bar 24 inserted through it and centered within the slot 12. One end of the bar extends about 0.5 inches from side wall 25, of the tube. The other end of the bar extends about 0.5 inches from side wall 27 of the tube and is used to mount a sample holding clip 26 which holds the tape tab for testing.

The shuttle is propelled in one longitudinal direction (i.e., from left to right in FIGS. 1A and 1B) by a long compression spring 28, such as a helical compression spring. The compression spring is positioned adjacent one of the end portions 13 of the tube, between the shuttle 20 and one of the end caps 14.

A spring loaded latch 30 is integrated into the tube at the compressed end 13. The latch holds the shuttle in place once the main spring 28 has been compressed. The end 13 with the latch is referred to as the loaded end. The latch 30 extends through an opening 31 in upper wall 33 of the tube. The latch 30 secures the shuttle in place against the compressed spring 28 by extending into the spring and loading the spring in a compressed position.

The clip 26 is attached to the end of the extended bar 24 extending from the shuttle and extending through opposed side walls 25, 27. The clip 26 is a spring actuated clamping device which purpose is to hold the tape tab for testing.

During use, a tape sample 50 (FIG. 2) is cut and applied to a substrate or test surface 32 as described in the ASTM method cited above. One end of the tape sample is doubled over forming a tape tab 52, wherein about one half of an inch of adhesive side 54 (which is applied directly to the surface 32) is disposed or folded onto a second portion of an adhesive side to create a non-stick tab 52. The tab is created to be used as a pulling point for the test. The device is held in the user's hands. The shuttle then is manually retracted and latched by latch 30 against compression spring 28. The shuttle is pulled to the loaded end 13 of the device, at which point the latch 30 is set to hold the shuttle 20 in position. The device is then placed onto the test surface 32, beside and parallel to the tape sample 50. The device is located in such a position as to have the clip 26 positioned directly over the tape tab 52. The tab is inserted into jaws or clamping opening 56 of the clip. At this point, the device is in the appropriate position and the sample is loaded and ready to perform the test.

To begin, the user applies downward pressure on the device with one hand to steady it for the test. Once the device is firmly held in position, the user flips the latch 30 to release the shuttle 20. The shuttle carries the clipped sample 50 from the loaded end 13 of the tube to the opposite end 14 of the tube. As this happens, the tape sample 50 is pulled (via tab 52 which is secured in clip 26) at a consistent 180° angle with respect to surface 32, and at a repeatable rate. Once the shuffle 20 reaches the end position, the tape sample can be removed from the clip for evaluation of the adhesion of the tape onto the work surface. The time to perform this procedure can take as little as 10-15 seconds, once the user is familiar with this operating procedure.

The device is designed to be a testing tool. Integrating a spring loaded rubber roller into one end of the device would convert the device into a dual purpose tool. This modification would also allow the user to perform the sample application part of the procedure. This is a critical part of the procedure and will make the removal part more accurate and repeatable. Adding this feature creates a tool that can both apply and remove the sample according to the test method.

By adding the electronic load cell to the shuttle and connecting it to a digital readout, the device could be enhanced even further. An electronic load cell adds force measurement to the testing process and provides a subjective result and a quantitative result.

The exemplary embodiment has been described with reference to the preferred embodiments. Obviously, modifications and alterations will occur to others upon reading and understanding the preceding detailed description. It is intended that the exemplary embodiment and appended claims be construed as including all such modifications and alterations.

The invention claimed is:

1. A tape test removal device, comprising:
    an elongated housing having a first end and a second end, wherein said housing comprises an elongated tube;
    a shuttle which slides along a longitudinal axis of said housing between said first end and said second end and is disposed within said housing;
    a biasing member adjacent said first end of said housing and positioned adjacent said shuttle member;
    said biasing member is secured in a first, compressed conformation; and
    a clip extending from said shuttle to hold a portion of a tape to be tested.

2. The tape test removal device of claim 1, further comprising end caps disposed at said first end and said second end of said housing.

3. The tape test removal device of claim 1, wherein said housing further comprises a slot extending through a side wall of said housing.

4. The tape test removal device of claim 3, said shuttle member further comprising a member extending through said slot.

5. The tape test removal device of claim 4, wherein said clip extends from said member.

6. The tape test removal device of claim 1, wherein said biasing member comprises a compression spring.

7. The tape test removal device of claim 6, wherein a latch secures said compression spring in a compressed position.

8. The tape test removal device of claim 7, wherein said latch extends through an opening in an upper wall of said housing.

9. The tape test removal device of claim 1, wherein said clip comprises clamping portions for holding a tab of a tab of a tape to be tested.

10. The tape test removal device of claim 9, wherein said biasing member is released from a compressed state thereby moving said shuttle between said first and second ends of said housing and said clip pulls said tab of said tape at a consistent 180 degree angle between said first and said second end of said housing.

11. A method of testing tape removal from a work surface, comprising:
    bending an end of said tape to form a tab on said end of said tape by having an adhesive side of said tape folded on itself;
    positioning a tape test removal device onto said work surface;

applying pressure to said device to firmly position it onto said work surface;
securing the tab within a clip extending from said device;
flipping a latch on said device to release a compression spring therein;
moving a shuttle holding said clip which is adjacent said spring from a first end to a second end of said device by expansion of said spring against said shuttle; and,
pulling the tape at a substantial 180 degree angle with respect to the work surface as the shuttle moves from the first end to the second end.

\* \* \* \* \*